(12) United States Patent
Pandya et al.

(10) Patent No.: US 10,939,898 B2
(45) Date of Patent: Mar. 9, 2021

(54) VASCULAR CLOSURE DEVICE

(71) Applicant: MERIL LIFE SCIENCES PVT. LTD., Vapi (IN)

(72) Inventors: Harshit Ganeshbhai Pandya, Valsad (IN); Rajnikant Gandal Vyas, Mumbai (IN); Pramod Kumar Minocha, Vapi (IN)

(73) Assignee: MERIL LIFE SCIENCES PVT. LTD., Vapi (IN)

( * ) Notice: Subject to any disclaimer, the term of this patent is extended or adjusted under 35 U.S.C. 154(b) by 335 days.

(21) Appl. No.: 15/688,859

(22) Filed: Aug. 28, 2017

(65) Prior Publication Data

US 2018/0055497 A1 Mar. 1, 2018

(30) Foreign Application Priority Data

Aug. 27, 2016 (IN) .............................. 201621029222

(51) Int. Cl.
*A61B 17/00* (2006.01)
*A61B 90/00* (2016.01)

(52) U.S. Cl.
CPC .. *A61B 17/0057* (2013.01); *A61B 2017/0042* (2013.01); *A61B 2017/00367* (2013.01); *A61B 2017/00455* (2013.01); *A61B 2017/00646* (2013.01); *A61B 2017/00654* (2013.01); *A61B 2017/00663* (2013.01); *A61B 2017/00778* (2013.01); *A61B 2090/0811* (2016.02)

(58) Field of Classification Search
CPC .......... A61B 2017/00367; A61B 2017/00584; A61B 2017/00455; A61B 2017/00778; A61B 17/0057; A61B 2090/0811
See application file for complete search history.

(56) References Cited

U.S. PATENT DOCUMENTS

| | | | | |
|---|---|---|---|---|
| 5,383,896 A | * | 1/1995 | Gershony | A61B 17/0057 604/103.03 |
| 5,531,759 A | * | 7/1996 | Kensey | A61B 17/0057 604/15 |
| 5,653,730 A | * | 8/1997 | Hammerslag | A61B 17/00491 128/898 |
| 6,110,184 A | * | 8/2000 | Weadock | A61B 17/0057 148/213 |
| 2012/0143245 A1 | * | 6/2012 | Tegels | A61B 17/0057 606/213 |

* cited by examiner

*Primary Examiner* — Shaun L David
*Assistant Examiner* — Christina C Lauer
(74) *Attorney, Agent, or Firm* — Kunzler Bean & Adamson, PC

(57) ABSTRACT

A vascular closure system is configured to seal an incision in a vessel of the patient's body. The system includes a slider that is moved from an initial position to a deployed position (that is, towards the puncture of the patient body), until the proximal end of the slider exposes a reference marker on an inner tube. This confirms the deployment of the closure element and completely expands or opens or pivots the closure element in the blood vessel.

8 Claims, 9 Drawing Sheets

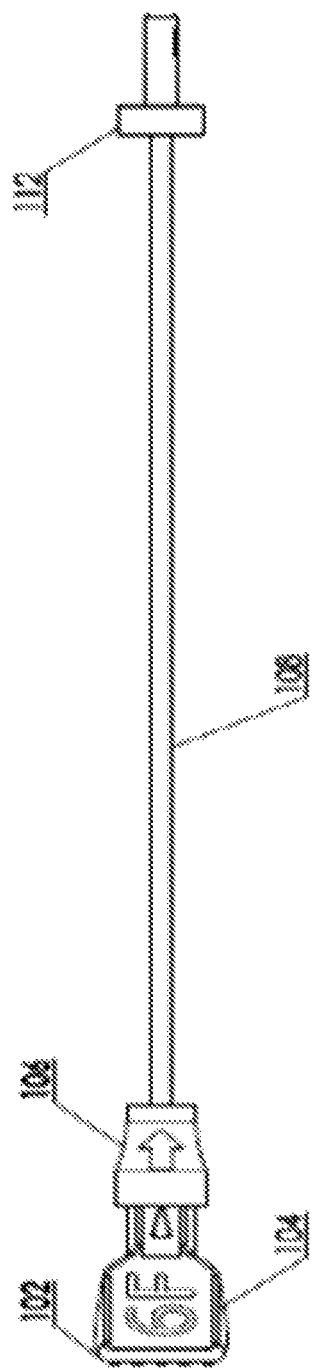

VASCULAR CLOSURE DEVICE

CROSS-REFERENCES TO RELATED APPLICATIONS

This patent application claims priority to Indian Patent Application Number 201621029222 entitled "VASCULAR CLOSURE DEVICE" and filed on Aug. 27, 2016 for Harshit Ganeshbhai Pandya, et al., which is incorporated herein by reference in its entirety, for all purposes.

FIELD OF INVENTION

The present disclosure relates to a medical device. More particularly, the present disclosure relates to a vascular closure device.

BACKGROUND

Nowadays, minimal invasive surgical procedures are common in operating a patient in a cathlab. Such minimal invasive surgery procedures are performed through a small incision in a hand or a leg of a patient to access the artery. During the surgical procedure, an "insertion sheath" is first inserted in the incision for providing a guide passage, which facilitates the insertion of the invasive devices. Upon completion of the procedure, the devices and insertion sheath are removed, leaving open the puncture site in the accessed vessel wall. Traditionally, for sealing the incision, external manual pressure is applied to the puncture site until clotting and wound sealing occur. During this process, the patient must remain bedridden for a substantial period after clotting to ensure closure of the wound. This procedure is also time consuming and expensive, requiring as much as an hour of a physician's or nurse's time. It is also uncomfortable for the patient and requires that the patient remain immobilized in the operating room, catheter lab, or holding area. In addition, a risk of hematoma exists from bleeding before hemostasis occurs. Although some wound closure systems may be available, they provide limited control and flexibility to the operator, which leads to improper or undesirable closure of the puncture site.

To overcome these drawbacks, vascular closure devices were developed. These devices achieved wound closure by deploying closure elements at the punctured site. Usual procedure requires introduction of an insertion sheath at the incision for insertion of invasive device(s) for surgical procedure. After surgical procedure, the insertion sheath is removed along with the invasive device(s) followed by insertion of an "introducer sheath" in the incision. The introducer sheath facilitates the insertion of the vascular closure device and deployment of closure elements.

As the insertion sheath is removed and a device compatible introducer sheath is introduced, a significant blood loss occurs. One way to mitigate such extra blood loss is by introducing a temporary inflated balloon for occlusion in the common femoral artery proximal to the sheath site, typically accessed from a contralateral femoral site. A simple low pressure inflation of the balloon creates flow stasis, allowing for sheath removal or exchange with minimum blood loss. However, such balloon placement is highly complex and may not be possible in complex incision profiles.

Hence, there is a need to minimize the blood loss during closure of the incision using the vascular closure device which is simple to use.

SUMMARY OF THE INVENTION

In accordance with an embodiment of an invention, the present disclosure relates to a vascular closure device. The vascular closure device is configured to seal an incision in a vessel (vascular incision) of the patient's body. The device includes a slider that is moved from an initial position to a deployed position (that is, towards the puncture of the patient body), until the proximal end of the slider exposes a reference marker on an inner tube. This confirms the deployment of the closure element and completely expands or opens or pivots the closure element in the blood vessel.

In an alternative embodiment, a vascular closure device configured to seal an incision in a vessel includes an outer tube having a lumen, a proximal end and a distal end; a slider coupled to the proximal end of the outer tube; an inner tube provided inside the lumen of the outer tube, the inner tube having a proximal end and a distal end; a reference marker provided on the proximal end of the inner tube; and a closure element positioned at the distal end of the outer tube such that the closure element pivots inside the vessel once the slider moves forward and positions the proximal end of the outer tube at the reference marker.

Other features of embodiments of the present disclosure will be apparent from accompanying drawings and from detailed description that follows.

BRIEF DESCRIPTION OF DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the disclosure is not limited to specific devices, methods and instrumentalities disclosed herein. Moreover, those in the art will understand that the drawings are not to scale. Wherever possible, like elements have been indicated by identical numbers.

FIG. 1C is an exemplary finished assembly of the vascular closure device 100 of FIG. 1A, in accordance with the first embodiment of the present disclosure;

DETAILED DESCRIPTION OF DRAWINGS

Prior to describing the invention in detail, definitions of certain words or phrases used throughout this patent document will be defined: the terms "include" and "comprise", as well as derivatives thereof, mean inclusion without limitation; the term "or" is inclusive, meaning and/or; the phrases "coupled with" and "associated therewith", as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; Definitions of certain words and phrases are provided throughout this patent document, and those of ordinary skill in the art will understand that such definitions apply in many, if not most, instances to prior as well as future uses of such defined words and phrases.

Wherever possible, same reference numbers will be used throughout the drawings to refer to same or like parts. Moreover, references to various elements described herein are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claims.

Particular embodiments of the present disclosure are described herein below with reference to the accompanying drawings, however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The present invention discloses a vascular closure device which is simple to use and achieves closure of a vascular puncture by deploying the closure elements within a puncture site/incision. It eliminates the drawbacks of conventional closure devices and results in effective hemostasis post interventional procedure. The vascular closure device of the present invention is designed to pass through the lumen of an introducer sheath that is already introduced in the body lumen of a patient for minimal invasive surgery procedures. Thus, haemostasis and blood loss due to sheath exchange is eliminated.

Figure 1A:
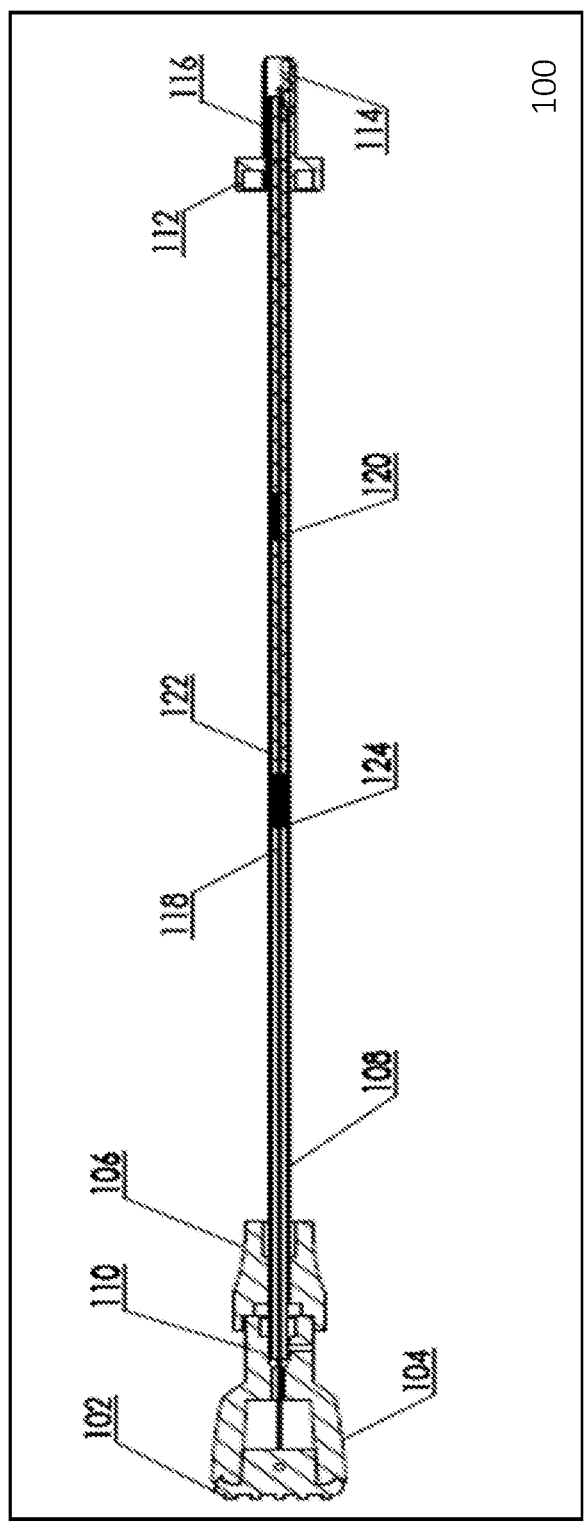
FIG. 1A is a first cross sectional view of an exemplary vascular closure device for closing a blood vessel of a patient, in accordance with a first embodiment of the present disclosure.
Figure 1B:
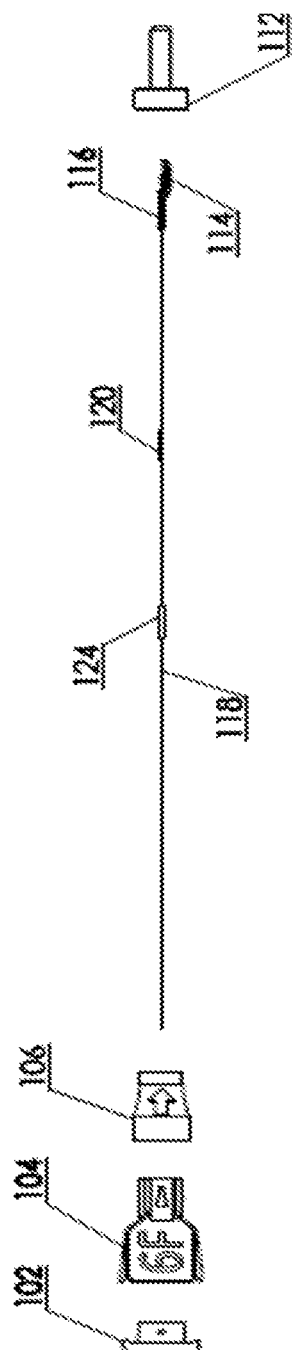
FIG. 1B depicts one or more markers provided on the suture 118 of FIG. 1A as an exemplary embodiment of the present disclosure.

FIGS. 1A & 1B show a cross-sectional view of an exemplary vascular closure device 100 for sealing an incision (not shown) in a patient body (not shown) in accordance with a first embodiment of the present disclosure. The vascular closure device 100 includes a cap 102, a hub 104, a slider 106, an outer tube 108, an inner tube 110, a gliding tube 112, a closure element 114, a hemostatic element 116, a suture 118, at least one deployment marker 120, a deployment tube 122 and a locking element 124. In an embodiment of the present invention, the vascular closure device 100 passes through the lumen of a corresponding introducer sheath already inserted in the body lumen of a patient for surgical procedures. The introducer sheath facilitates the passage of an invasive device(s) as well as a vascular closure device through its lumen, thus eliminating the need for two separate sheaths.

The cap 102 is removably coupled to the proximal end of the hub 104 and serves to hold the suture 118. For example, the inner surface of the cap 102 includes an aperture coupled to a suture 118 through a knot (not shown). However, the cap 102 may be coupled to the suture 118 via any other coupling methods, such as, but not limited to, gluing the suture 118 to the cap, integrating the suture 118 with the cap 102 while manufacturing the vascular closure device 100, etc. In an alternative embodiment, the cap 102 may include a protrusion (not shown) to couple the suture 118. The suture 118 may be made of any synthetic absorbable material, such as, but not limited to, polyglactin 910, polyglycolic acid, polydioxanone, polyglecaprone and the like. In an embodiment, the cap 102 and the hub 104 may integrally couple with the suture 118 to form a single piece structure. The cap 102 can be made of ABS, polycarbonate or any other polymer.

The hub 104 serves as a housing for the coupling formed between the suture 118 and the cap 102 and enables the user to hold the vascular closure device 100 while deploying it in the lumen of introducer sheath. As explained above, to the proximal end of the hub 104, the cap 102 is coupled while at a distal end of the hub 104, the slider 106 is slidably coupled. The proximal end of the hub 104 is coupled to the cap 102 through a suitable coupling mechanism, such as, but not limited to, a press-fit through a dovetail notch, an ultrasonic welding process, or a gluing process. Further, the hub 104 has a hollow profile which is integrally coupled to the external surface of the inner tube 110. The cap 102 and the hub 104 may be integrally manufactured or provided as two separate pieces assembled together.

The slider 106 facilitates the deployment of the closure element 114 and/or hemostatic element 116 in an incision. The hemostatic element 116 is positioned proximate to the closure element 114, and deployed to the incision along with the closure element 114. The closure element 114 and/or the hemostatic element 116 may be made of bio-degradable or bio-resorbable materials to facilitate dissolution of the same in the patient body over a period of time. The hemostatic element 116 may include a collagen matrix, gelatin, synthetic collagen, natural hemostatic element and the like.

In this first embodiment, as depicted, the proximal end of the slider 106 is operatively coupled (for example, slidably coupled, locked, etc.) to the distal end of the hub 104 such that in the initial position, the proximal end of the slider 106 surrounds the distal end of the hub 104. Alternately, the slider 106 may be coupled (or locked or slidably locked) to the outer tube. In FIG. 1A, the slider 106 is depicted in an initial position. The distal end of the slider 106 is integrally coupled to the proximal end of the outer tube 108. Thus, during deployment, the slider 106 may slide forward and/or glide the outer tube 108 over the inner tube 110 and would then be referred to be in a deployed position. In an alternate embodiment, during deployment, the hub 104 may be pulled backwards and/or glide the inner tube 110 inside the outer tube 108.

An intermediate section of the slider 106 may include a slider marking that indicates the direction of movement of the slider 106 for deploying the closure element 114 and/or hemostatic element 116 as shown in FIG. 1B. In one embodiment, the slider marking may be inscribed in the intermediate section. In other embodiment, the slider marking may be embossed on the intermediate section.

In an embodiment, the diameter of the proximal end of the slider 106 is higher than that of the distal end. The diameter ratio between the proximal end and the distal end of the slider may be about 2:1. As the diameter of the proximal end of the slider 106 is larger than the diameter of the distal end (also referred as slider extension) of the hub 104, the slider 106 slides over a slider extension provided with the hub 104.

The outer tube 108 acts as a sheath and protects the inner tube 110. In an embodiment, the outer tube 108 may be coaxially placed with the inner tube 110 such that the inner tube 110 is placed in the lumen of the outer tube 108. In an embodiment, the diameter of the outer tube 108 is such that that it conforms to the diameter of an introducer sheath and is able to pass through the lumen of introducer sheath.

The inner tube 110 is integrally coupled to the hub 104 at its proximal end, while at its distal end, the closure element 114 and the hemostatic element 116 are positioned. In an embodiment, the inner tube 110 includes a slit at its distal end to facilitate the accommodation of the closure element 114 and hemostatic element 116. The length of the slit may be about 10 mm to 30 mm. In an embodiment, the length of the slit is 15 mm.

The inner tube 110 is provided with a reference marker (not shown) on its outer surface. The reference marker is provided towards the proximal end of the inner tube 110 and serves to indicate pivoting of the closure element 114 on the movement of the slider 106 to this position.

The inner tube 110 also contains a lumen through which the suture 118 passes. Towards the distal end of this lumen, a deployment tube 122 is positioned. The deployment tube 122 is a hollow tube with a length that is a fraction of the length of the inner tube 110. In an embodiment, at least one end of the deployment tube 122 has a filleted structure. During the introduction of the vascular closure device 100, the filleted structure facilitates effective translation of the deployment tube 122 without any stress factor. As shown in FIG. 1A, the suture 118 passes partly through the lumen of the inner tube 110 and partly through the lumen of the deployment tube 122.

The length of the inner tube 110 may be selected based on the application for which the vascular closure device 100 is used. In an embodiment, the length of the outer tube 108 and the inner tube 110 is nearly same. The outer tube 108 and the inner tube 110 may be made of a flexible material, such as, but not limited to, HDPE, Apex, Nylon and the like.

The gliding tube 112 helps in ease of delivering the vascular closure device 100 inside the lumen an introducer sheath by smoothly gliding over the external surface of the outer tube 108. Thus, gliding tube 112 is slidably coupled to the distal end of the outer tube 108. The gliding tube 112 is hollow with a hub 104 at its proximal end while the distal end of the gliding tube 112 has an opening. In one embodiment, the gliding tube 112 may be transparent and made of any polymer material, such as polycarbonate, ABS or polypropylene and the like. When the vascular closure device 100 is inserted in a sheath 300 (FIG. 4A), the gliding tube 112 serves to protect the closure element 114 and the hemostatic element 116 when delivered through a hub of an introducer sheath. The sheath 300 facilitates the passage of an invasive device(s) as well as a vascular closure device both through its lumen thus eliminating the need of two separate sheaths.

FIGS. 1A & 1B depict various markers provided on the suture 118 as an exemplary embodiment. At the distal end of the suture 118, the closure element 114 followed by the hemostatic element 116 is attached. Further, the suture 118 is provided with one or more deployment markers 120 that indicate complete deployment of the hemostatic element 116. The deployment markers 120 may be made of medical grade ink.

Optionally, the suture 118 is coupled to a locking element 124, which locks the movement of the deployment tube 122 in the inner tube 110. Further, the locking element 124 ensures that the entire suture 118 is deployed in the incision of the patient body.

Referring to FIG. 1C, the present invention discloses an exemplary 6F (French) vascular closure device 100. However, the present disclosure is not limited to 6F (6 French) vascular closure device 100 and a person skilled in the art will understand that the teachings of the present disclosure apply to other vascular closure devices also.

Figure 1D:
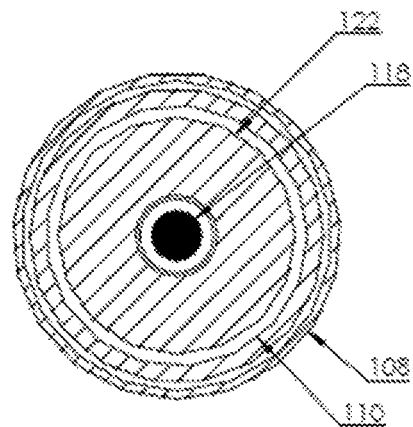
FIG. 1D is a second cross sectional view of the vascular closure device 100 of FIG. 1A, in accordance with the first embodiment of the present disclosure.

FIG. 1D is a radial cross sectional view of the vascular closure device 100 in accordance with the first embodiment of the present disclosure. It is evident that the suture 118 is provided in the lumen of the deployment tube 122 which in turn is provided in the lumen of the inner tube 110. Finally, the inner tube 110 is provided in the lumen of the outer tube 108. It should be noted that the deployment tube 122 is shorter in length compared to the inner tube 110 and is provided towards the distal end of the inner tube 110.

Figure 1E:
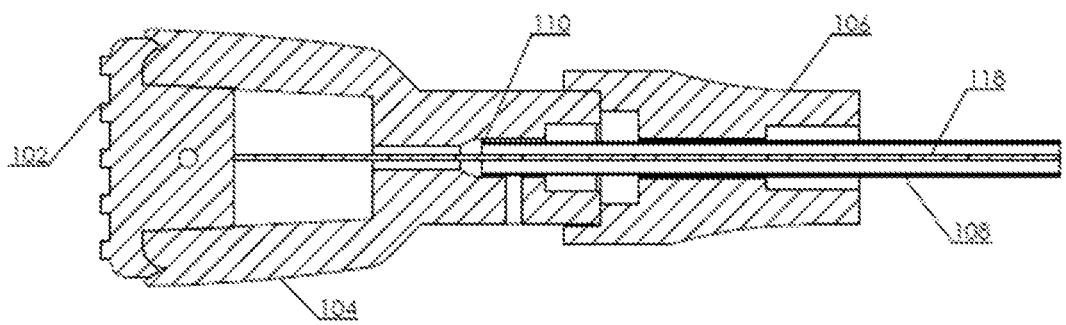
FIG. 1E is an enlarged view of the vascular closure device 100 of FIG. 1A, in accordance with the first embodiment of the present disclosure.

FIG. 1E is an enlarged view of the proximal end of the vascular closure device 100 in accordance with the first embodiment of the present disclosure. It is clearly shown that the cap 102 sits in the hollow profile of the proximal end of the hub 104. Further, the inner tube 110 is integrally coupled to the distal end of the hub 104 while the outer tube 108 is integrally coupled to the slider 106.

Figure 2:
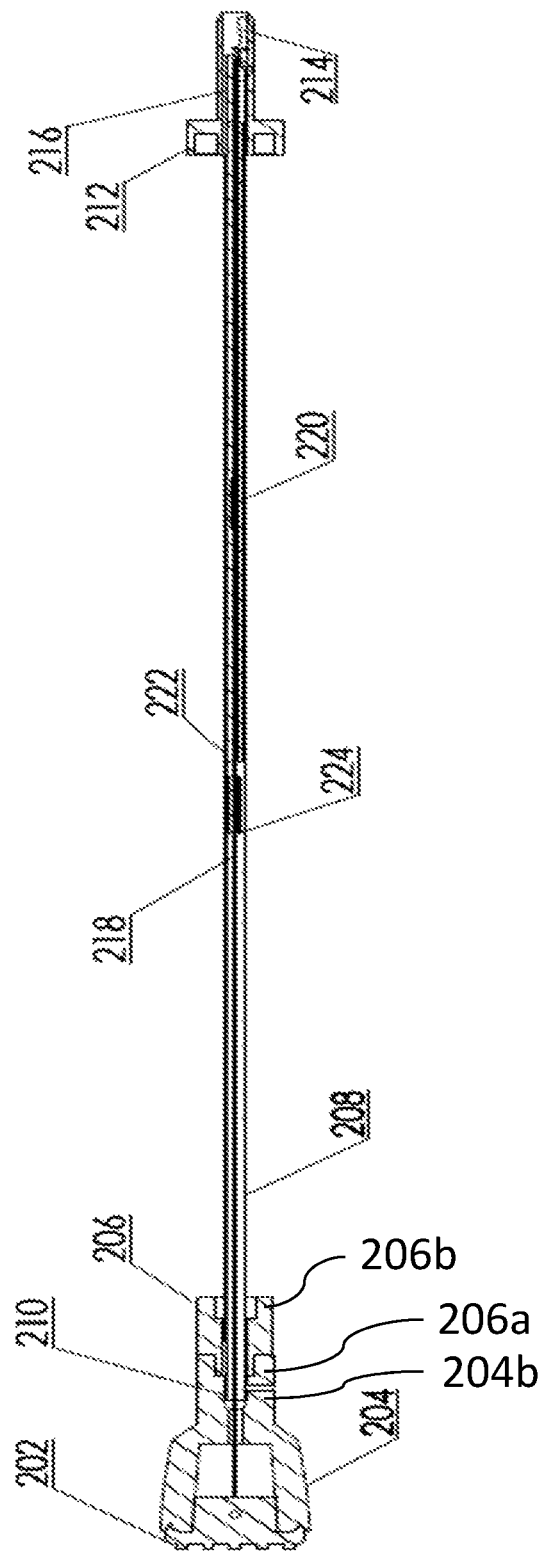
FIG. 2 is an exemplary sectional view of the vascular closure device, in accordance with a second embodiment of the present disclosure.

FIG. 2 shows an alternative embodiment of the vascular closure device 100. In this alternate embodiment, the diameter of the proximal end 206a of the slider 206 is lower than that of the distal end 206c. The diameter ratio between the proximal end 206a and the distal end 206c of the slider 206 may be about 1:2. As the diameter of the proximal end 206a of the slider 206 is lesser than the diameter of the slider extension 204b of the hub 204, the slider 206 slides inside the hub 204. Further, the slider 206 may have a splined connection with the hub 204 for effective translation, thus avoiding any slip in the connection. Details of the assembly of the remaining parts are the same as FIGS. 1A-1B and can be referred thereto.

Figure 3:
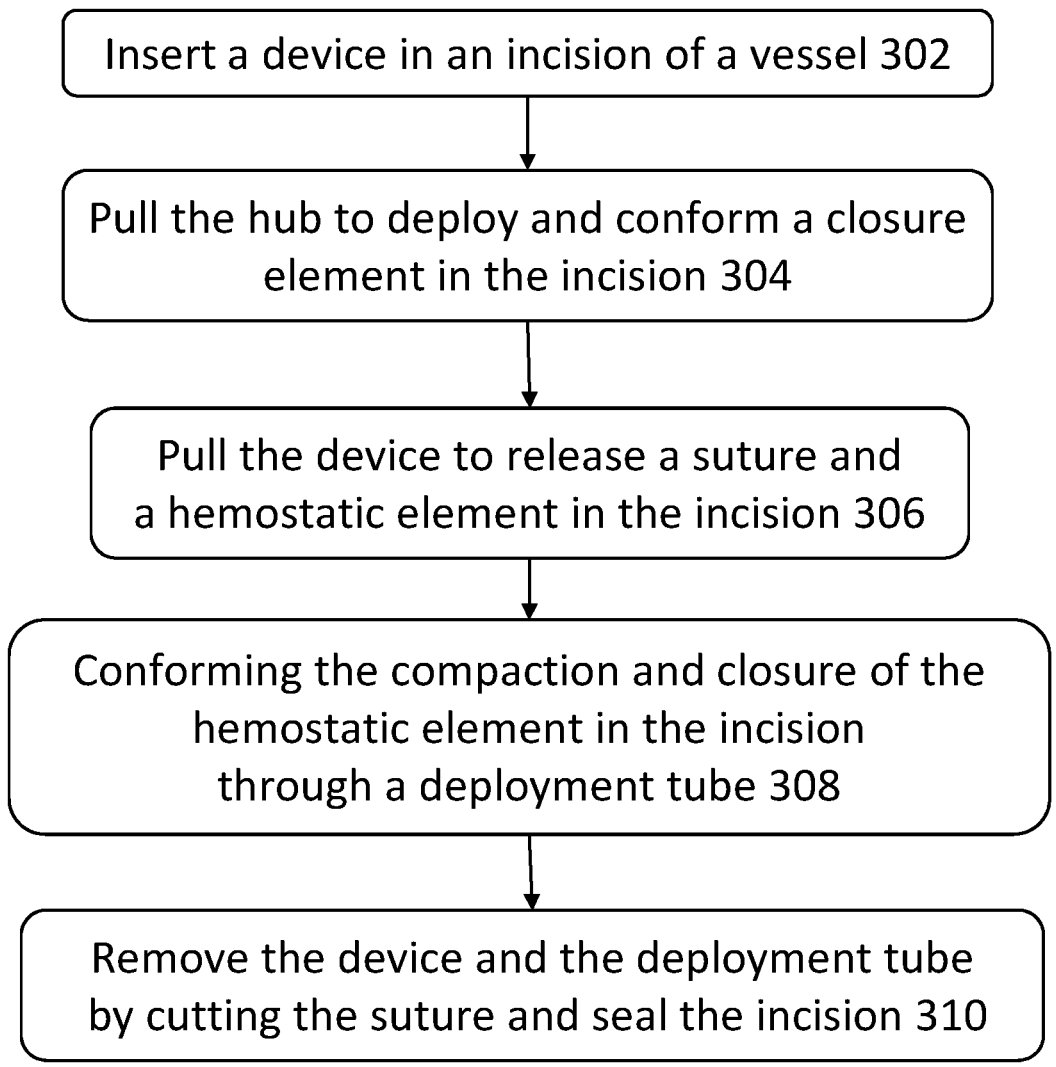
FIG. 3 is a flow chart for deploying the vascular closure device, in accordance with an embodiment of the present disclosure.
Figure 4A:
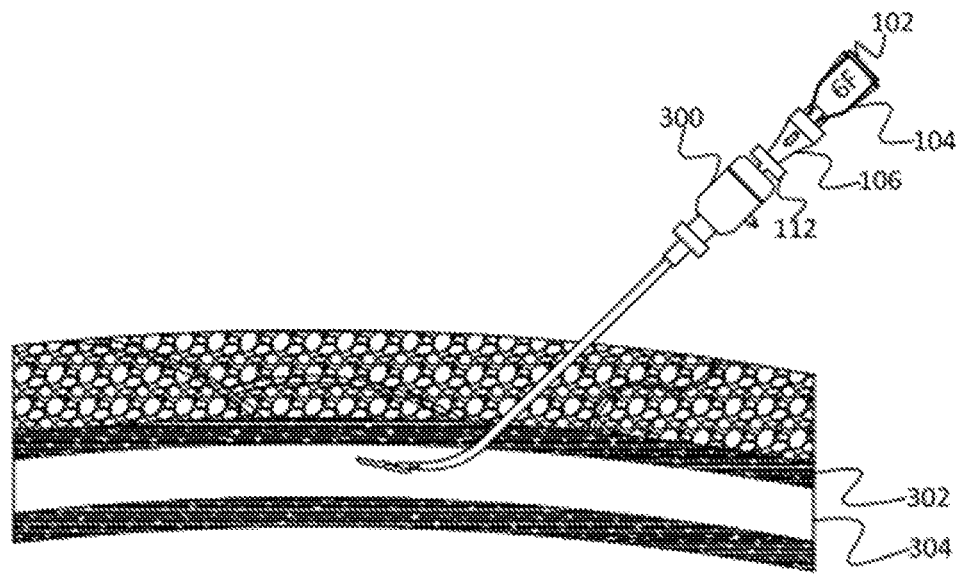
FIGS. 4A-4F show an exemplary illustrations of the various steps of the flowchart of FIG. 3, in accordance with an embodiment of the present disclosure.

FIG. 3 shows a flowchart illustrating an exemplary working of the vascular closure device 100. At step 302, the vascular closure device 100 is introduced inside the lumen of a sheath 300, which may have been inserted in an incision for minimally invasive surgery. The distal end of the gliding tube 112 of the vascular closure device 100 is inserted in a hub opening of the sheath 300. The slider and the hub assembly are mounted on the sheath 300 such that the distal end of the slider 106 is placed adjacent to the proximal end of the gliding tube 112. In this position, the outer tube 108 is placed inside the lumen of the sheath 300. Further, once the gliding tube 112 is locked with the sheath 300, the closure element 114 is extended out of the gliding tube 112. This initial position is depicted in FIG. 4A. In this position, some distance may be maintained between the surface of skin of the patient and the sheath 300.

Figure 4B:
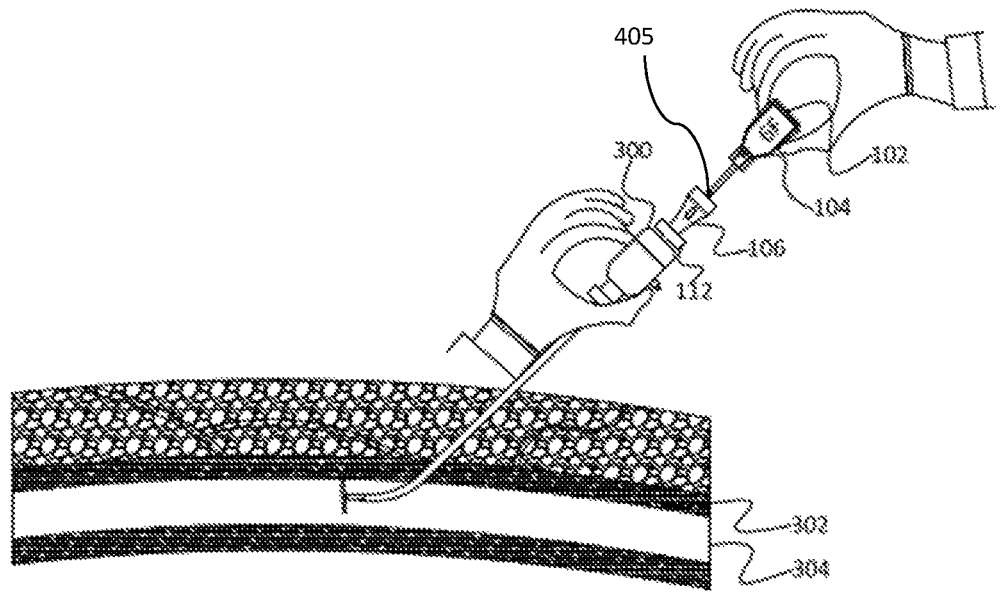

At step 304, the slider 106 is pushed forward such that the outer tube 108 slides over the inner tube 110 until a reference marker 405 on the inner tube 110 is exposed (FIG. 4B). Or, the slider slidably locked to a gliding tube until the reference marker 405 on the inner tube 110 is exposed. Alternately, the hub is pulled until the reference marker 405 on the inner tube 110 is exposed. In this position, the closure element 114 pivots (or expand or opens) and sits parallel or at an angle to the punctured artery, hence, the chances of the closure element 114 being withdrawn with the vascular closure device 100 are negated. This may be referred to as the deployed position of the closure element 114. The element 114 may be deployed at an angle or be parallel to the incision. In an embodiment, the angle may vary from 45 degrees to 90 degrees.

Figure 4C:
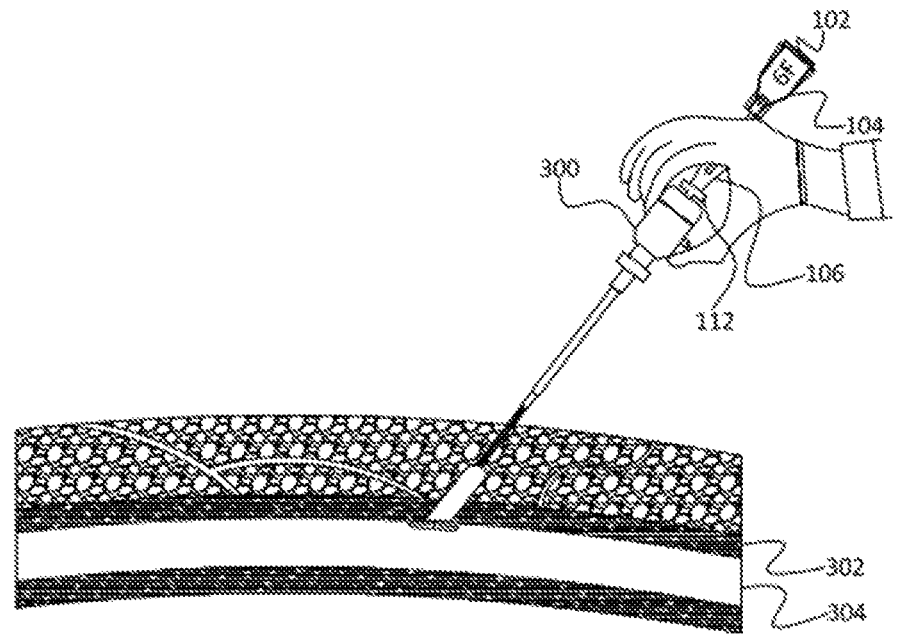

At step 306, the user pulls the sheath 300, the hub 104 and the slider 106 proximally. As the sheath 300 is pulled from the incision of the patient's body, the hemostatic element 116 is released outside the incision of the patient body as shown in FIG. 4C.

Figure 4D:
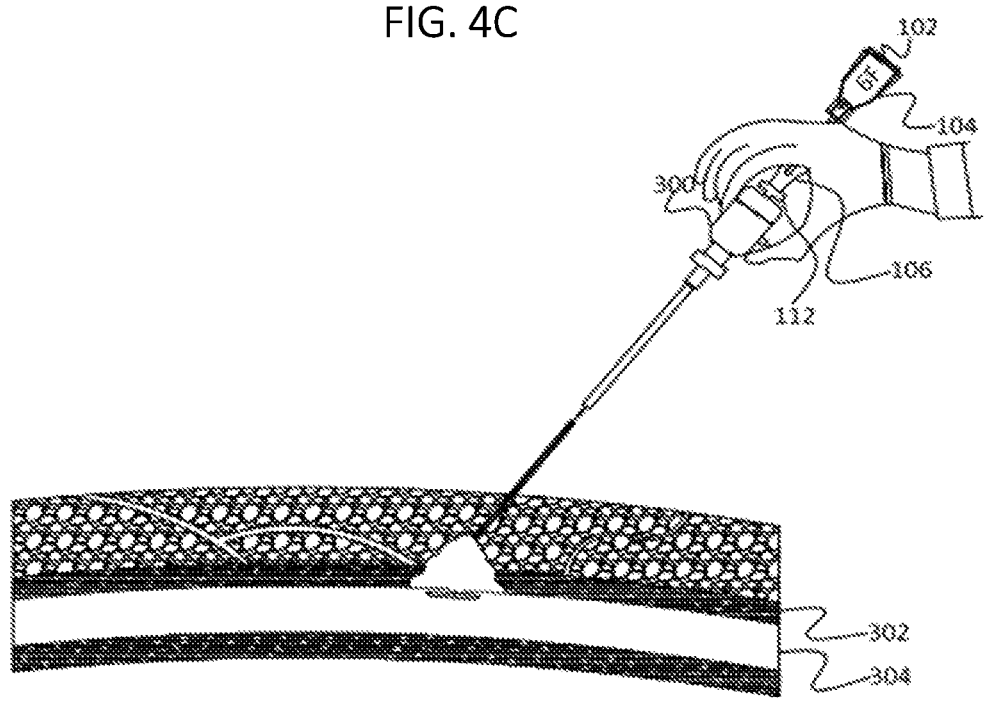

At step 308, the sheath 300 along with the hub 104 and slider 106 is further pulled from the incision of the patient's body, until the deployment tube 122 is exposed completely from the inner tube 110 as shown in FIG. 4D. This indicates that the hemostatic element 116 is completely released.

Figure 4E:
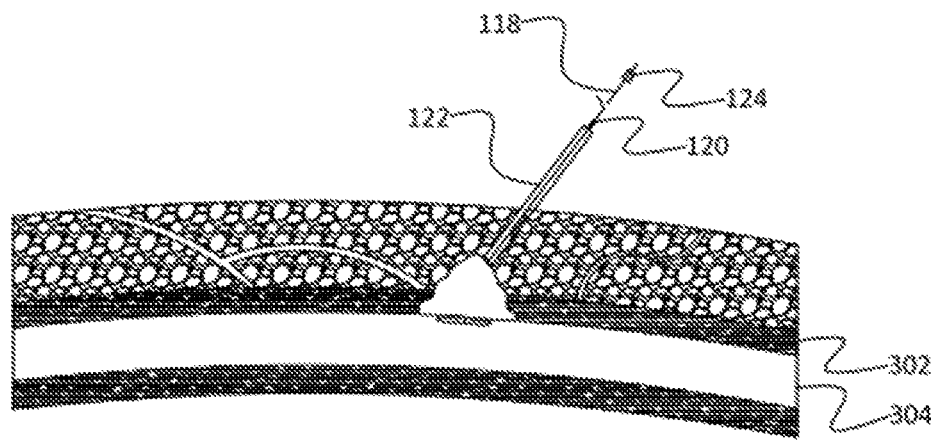

Upon the release of the hemostatic element 116, the deployment tube 122 is pushed towards the incision of the patient for compacting the hemostatic element 116 at the incision of the patient until the deployment marker 120 is exposed (shown in FIG. 4E). The deployment tube 122 may be pushed manually. The deployment marker 120 is provided on the suture 118 and covered/hidden under the deployment tube 122. The deployment marker 120 is positioned in such a way that exposure of the deployment marker indicates closure of the incision in the patient body.

Figure 4F:
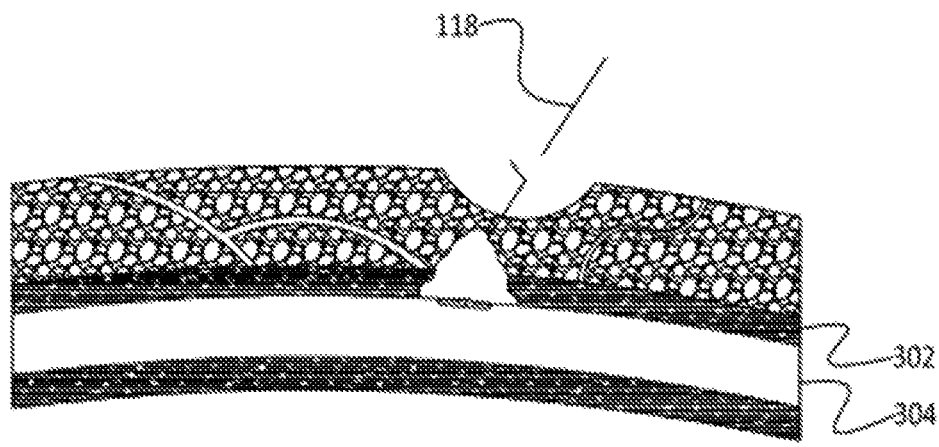

At step 310, upon confirmation of the vascular closure once the deployment marker 120 is exposed, the user may cut the suture between the locking element 124 and the deployment marker 120 and may remove the vascular closure device 100 as shown in FIG. 4F.

In a preferred embodiment, the closure element 114 may have a boat-shaped structure and positioned in the inner tube 110. In other embodiments, the closure element may have any shape, such as, but not limited to, a rectangular shape, a brick shape, circular sheet shape and the like. In an embodiment, when the slider 106 is moved from the initial position to the deployed position, the closure element 114 is deployed in the incision of the patient body at a pivoted angle. During deployment of the closure element, the closure element is pre-configured to pivot from 45 degrees to 90 degrees, such that effective closure of the incision is obtained in the patient body.

The above mentioned steps are exemplary working mechanism of the vascular closure device 100. However, the user may vary the method of operation in accordance with the requirements of the patient.

From the above, it may be seen that the entire assembly as well as operation of the device is highly simplified and provides accurate sealing of the incision. Due to this simplified assembly, it is very easy for a surgeon to use the device for the intended purpose.

Various modification or additions to the above disclosure are feasible and fall within the teachings of the present disclosure. For example, the proximal end of the outer tube may be coupled to the proximal end of the slider or the inner tube may be coupled to the distal end of the hub, etc.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A vascular closure device configured to seal an incision in a vessel, the device comprising:
    a hub;
    an outer tube having a lumen, a proximal end and a distal end;
    a slider coupled to the proximal end of the outer tube or distally to the hub;
    an inner tube provided inside the lumen of the outer tube, the inner tube having a proximal end and a distal end, the proximal end of the inner tube coupled to the hub;
    a reference marker provided on the proximal end of the inner tube such that the reference marker becomes exposed in response to the hub being held and the slider being pushed;
    a deployment tube provided inside the lumen of the inner tube, the deployment tube having a lumen, the deployment tube being completely exposed in response to the hub and the slider being retracted and a deployment marker being exposed in response to pushing the deployment tube toward a vessel;
    a hemostatic element provided towards the distal end of the outer tube and held in position via a suture passing through the lumen of the deployment tube; and
    a closure element coupled to the distal end of the hemostatic element and the suture,
    wherein the closure element pivots or opens or expands inside the vessel once the slider moves forward and positions the proximal end of the outer tube at the reference marker such that the reference marker becomes exposed.

2. The device as claimed in claim 1 wherein the deployment tube conceals the deployment marker.

3. The device as claimed in claim 2 wherein exposure of the deployment marker confirms compaction of the hemostatic element.

4. The device as claimed in claim 1 wherein the hub is slidably coupled with the outer tube.

5. The device as claimed in claim 1 wherein the suture is provided at least partially inside the inner tube.

6. A method of sealing an incision of a vessel, the method comprising the steps of:
    inserting a gliding tube partially or fully in an introducer sheath, the introducer sheath facilitates introduction of invasive devices;
    pushing an outer tube of the vascular closure device inside a lumen of the introducer sheath till a slider and hub of the vascular closure device aligns with the gliding tube;
    holding the hub and pushing the slider of the vascular closure device simultaneously until a reference marker is exposed on an inner tube of the vascular closure device;
    retracting the hub and the slider of the vascular closure device along with the introducer sheath till a deployment tube of the vascular closure device is completely exposed; and
    pushing the deployment tube towards the vessel until a deployment marker is exposed, thereby indicating complete deposition of a hemostatic element, thereby sealing an incision of a vessel.

7. A method of sealing an incision of a vessel, the method comprising the steps of
    inserting a gliding tube partially or fully in an introducer sheath, the introducer sheath facilitates introduction of invasive devices;
    pushing an outer tube of the vascular closure device inside a lumen of the introducer sheath till a slider and hub of the vascular closure device aligns with the gliding tube;
    holding the slider and pulling the hub of the vascular closure device simultaneously until a reference marker is exposed on an inner tube of the vascular closure device;

retracting the hub and the slider of the vascular closure device along with the introducer sheath till a deployment tube of the vascular closure device is completely exposed; and pushing the deployment tube towards the vessel until a deployment marker is exposed, thereby indicating complete deposition of a hemostatic element, thereby sealing an incision of a vessel.

8. A vascular closure device assembly configured to seal an incision in a vessel, the assembly comprising:

an introducer sheath having a lumen, the introducer sheath facilitates passage of an invasive device as well as a vascular closure device through its lumen, the vascular closure device comprising:

a hub;

an outer tube having a lumen, a proximal end and a distal end;

a slider coupled to the proximal end of the outer tube or distally to the hub;

an inner tube provided inside the lumen of the outer tube, the inner tube having a proximal end and a distal end, the proximal end of the inner tube coupled to the hub;

a reference marker provided on the proximal end of the inner tube such that the reference marker becomes exposed in response to the hub being held and the slider being pushed;

a deployment tube provided inside the lumen of the inner tube, the deployment tube having a lumen, the deployment tube being completely exposed in response to the hub and the slider being retracted and a deployment marker being exposed in response to pushing the deployment tube toward a vessel;

a hemostatic element provided towards the distal end of the outer tube and held in position via a suture passing through the lumen of the deployment tube; and a closure element coupled to the distal end of the hemostatic element and the suture, wherein the closure element pivots or opens or expands inside the vessel once the slider moves forward and positions the proximal end of the outer tube at the reference marker such that the reference marker becomes exposed.

* * * * *